United States Patent
Kim et al.

(10) Patent No.: US 9,568,438 B1
(45) Date of Patent: Feb. 14, 2017

(54) SINGLE-CAMERA ANGLED CONVEYANCE IMAGING METHOD AND APPARATUS FOR WHOLE-SURFACE INSPECTION OF ROTATING OBJECTS

(71) Applicants: The United States of America, as represented by the Secretary of Agriculture, Washington, DC (US); Republic of Korea, as represented by the Administrator of Rural Development Administration, Jeollabuk-do (KR)

(72) Inventors: Moon S. Kim, Silver Spring, MD (US); Kuanglin Chao, Ellicott, MD (US); Alan M. Lefcourt, Elkridge, MD (US); Kangjin Lee, Hwasung-si (KR); Sukwon Kang, Seoul (KR); Diane E. Chan, Odenton, MD (US)

(73) Assignees: The United States of America, as represented by the Secretary of Agriculture, Washington, DC (US); Republic of Korea, as represented by the Administrator of Rural Development Administration, Jeollabuk-do (KR)

( * ) Notice: Subject to any disclaimer, the term of this patent is extended or adjusted under 35 U.S.C. 154(b) by 685 days.

(21) Appl. No.: 13/782,461

(22) Filed: Mar. 1, 2013

(51) Int. Cl.
*H04N 7/18* (2006.01)
*G01N 21/95* (2006.01)

(52) U.S. Cl.
CPC .................. *G01N 21/95* (2013.01)

(58) Field of Classification Search
None
See application file for complete search history.

(56) References Cited

U.S. PATENT DOCUMENTS

| | | | |
|---|---|---|---|
| 4,726,898 A | 2/1988 | Mills et al. | |
| 4,825,068 A * | 4/1989 | Suzuki | B07C 5/10 250/223 R |
| 6,659,287 B1 * | 12/2003 | Hawkins | B07C 5/36 198/483.1 |
| 6,691,854 B1 | 2/2004 | De Greef | |
| 6,888,082 B1 | 5/2005 | Blanc | |
| 7,280,198 B2 | 10/2007 | Blanc | |
| 7,787,111 B2 * | 8/2010 | Kim | G01N 21/55 250/461.1 |
| 2007/0042096 A1 * | 2/2007 | Suasin | A23N 7/00 426/482 |
| 2011/0142201 A1 * | 6/2011 | Eberhard | G01V 5/0008 378/57 |

FOREIGN PATENT DOCUMENTS

GB    WO 9415173 A1 *   7/1994   ............. G01B 11/25

* cited by examiner

*Primary Examiner* — James M Anderson, II
(74) *Attorney, Agent, or Firm* — John D. Fado; Robert D. Jones

(57) ABSTRACT

The single-camera angled conveyance inspection method and apparatus includes upwardly and downwardly angled conveyance mechanisms positioned within an instantaneous field of view of a digital line scan camera. As a rotating object is moved over the conveyances by a helical guide, the camera obtains images of the object and communicates the images to a processor. The processor assembles a reflectance and fluorescence image of the object including detected defects and/or contamination on the outer surface of the object.

17 Claims, 1 Drawing Sheet

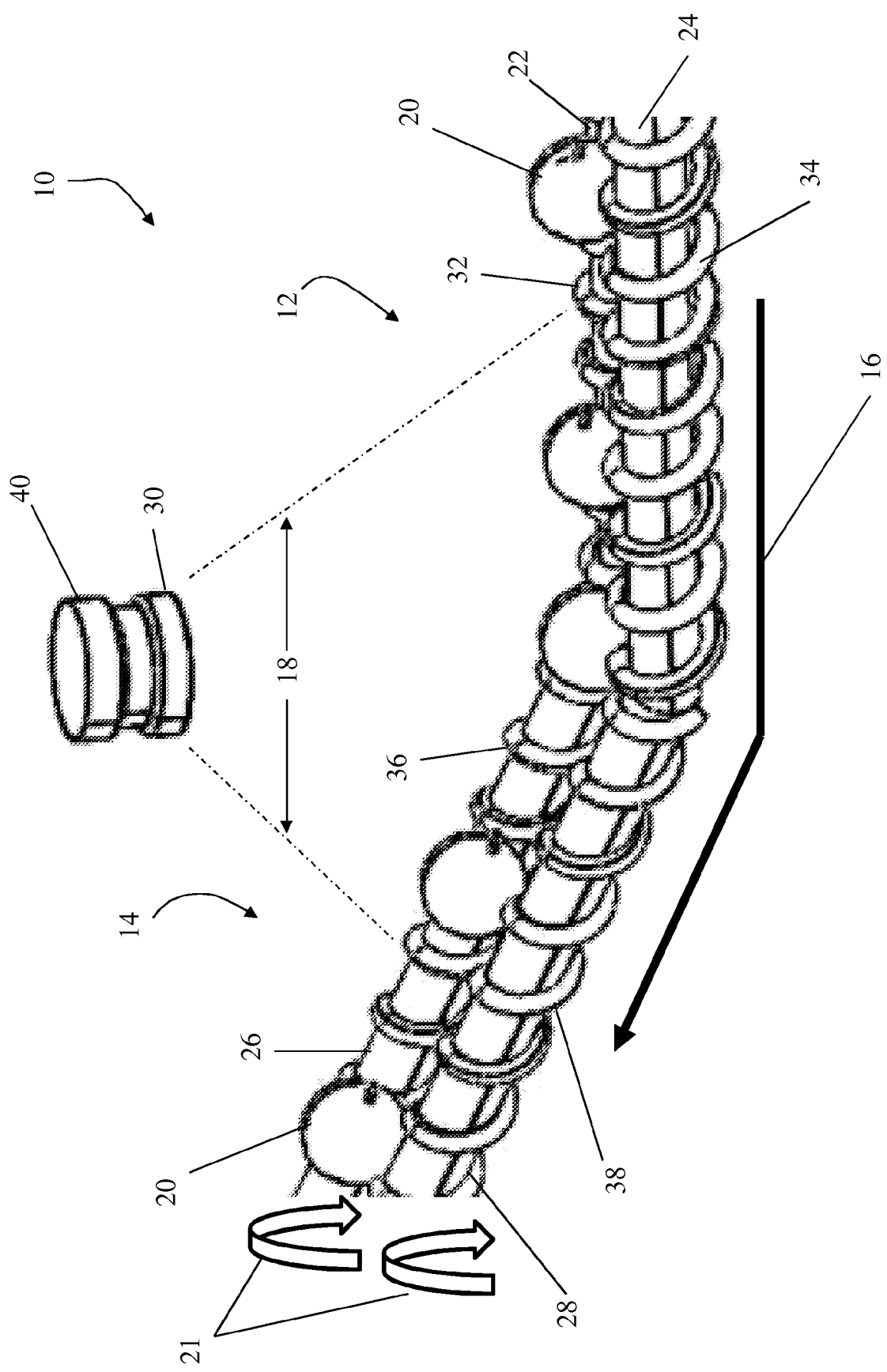

SINGLE-CAMERA ANGLED CONVEYANCE IMAGING METHOD AND APPARATUS FOR WHOLE-SURFACE INSPECTION OF ROTATING OBJECTS

FIELD OF THE INVENTION

The disclosed method and apparatus relates to imaging a whole surface of a rotating object. Specifically, the method and apparatus relates to imaging a whole surface of a spheroidal rotating object using an angled conveyance system.

BACKGROUND OF THE INVENTION

Currently, the most common method for inspecting essentially spherical objects (such as fruits and vegetables) requires production line personnel to visually inspect the objects as the objects are conveyed along a production line. However, the human visual inspection process is both slow and unreliable, and some contaminating materials that pose serious health risks are hard to visually identify—particularly on a moving production line. Further, inspectors do not systematically rotate each individual object so that all surfaces of the inspected object are visible to the inspector.

To address these vulnerabilities, fruit and vegetable processors are developing machine vision systems to identify defects and contaminants. One example of such a system is disclosed in U.S. Pat. No. 7,787,111 to Kim et al. (hereinafter "Kim"), which is hereby incorporated by reference. The system disclosed by Kim comprises a rapid online line-scan imaging system capable of both hyperspectral/multispectral reflectance and fluorescence imaging. Reflectance imaging at multiple wavelengths detects quality and surface anomalies, while fluorescence imaging at multiple wavelengths is used to detect fecal matter and other types of bacterial contamination.

Although these examination tools and techniques improve the inspection process, the imaging systems are complex and expensive. For example, in accordance with Kim, multiple cameras may be required to adequately inspect all surfaces of a spheroid. Further, the data collected from all cameras must be processed and synchronized to accurately portray the three-dimensional spheroidal object. For maximum efficiency and minimal error, synchronization and processing should occur almost immediately to ensure that defective objects are not comingled with non-defective items.

The method and apparatus described herein simplifies the imaging process by providing an imaging system that utilises only one camera and associated processor. The system quickly and effectively gathers the imaging data for the whole surface of an inspected object and allows for the identification of essentially all surface defects as well as selected types of bacterial (fecal) contamination.

SUMMARY OF THE INVENTION

This disclosure is directed to a method and apparatus for inspecting objects, preferably spheroidal fruits and vegetables traveling along a conveyor line. In accordance with the method and apparatus, a rotating object is directed down a downwardly-angled conveyance and up an upwardly-angled conveyance. The downwardly and upwardly angled conveyances comprise a plurality of members that rotate the object as the object moves over the conveyances. A helical guide(s) encircles each of the members so that the helical guides direct the object forward along the conveyances. A digital line scan camera is positioned so that as the object moves over the conveyances, the object moves through the instantaneous field of view (IFOV) of the camera. The camera communicates images of the object to a processor. The processor receives the images and produces image data for the object. The inspection system is structured so that the object is retained or rejected based on the image data produced by the processor.

BRIEF DESCRIPTION OF THE DRAWINGS

FIG. 1 is an elevational view of the single-camera angled conveyance inspection system.

DETAILED DESCRIPTION OF PREFERRED EMBODIMENTS

As generally shown in FIG. 1, the method and apparatus described herein comprises an inspection system 10 that includes a downwardly angled conveyance mechanism 12 and a corresponding upwardly angled conveyance mechanism 14. As a rotating object 20 moves in the direction of travel indicated by the arrow 16, the object 20 moves into the IFOV (as defined by the area 18) of a digital line scan camera 30. The processor 40 communicating with the camera 30 collects and processes a line scan images of the object 20 to determine whether the object 20 should be rejected or retained for further processing.

As best shown in FIG. 1, in the preferred embodiment, the downwardly angled conveyance 12 is comprised of first 22 and second 24 downwardly angled elongated members, and the upwardly angled conveyance 14 is comprised of essentially identical first 26 and second 28 upwardly angled elongated members. The downwardly angled 12 and upwardly angled 14 conveyance mechanisms are essentially mirror images of one another.

The downwardly angled conveyance 12 in combination with the upwardly angled conveyance 14 forms a "V" shape. The exact angle of the downward 12 and upward 14 conveyances relative to each other (and to horizontal) may be varied as required to achieve the best results for a specific application. The angular travel of the objects 20 along the conveyances 12, 14 (relative to the IFOV 18 of the camera 30) functions to expose surfaces of the object 20 that would not otherwise be visible to a conventionally-positioned overhead camera on a traditional horizontal conveyor. The increased surface area exposure enables the system 10 to more thoroughly inspect the outer surface of the objects 20 and thereby detect defects and contamination that might otherwise go undetected.

The elongated members 22, 24, 26, 28, may be smooth or textured, as required. As best shown by the arrows 21, the members 22, 24, 26, 28 rotate in the same direction so that the inspected object 20 is continuously rotated as it moves down the downwardly angled conveyance 12 and up the upwardly angled conveyance 14. The members 22, 24, 26, 28 include helical guides 32, 34, 36, 38 that encircle the respective members 22, 24, 26, 28 and guide the inspected objects 20 forward through the inspection system 10. In the preferred embodiment, the inspected object 20 is a spheroidal food product, such as a fruit or vegetable.

Although not specifically shown in the drawings, the inspection system 10 includes a lighting system that illuminates the rotating object 20, as disclosed (for example) in Kim. Specifically, the lighting system may include a quartz-tungsten halogen (QTH) reflectance lamp. Near infrared (NIR) light emitting diodes (LEDs) or an NIR laser with (or without) a long pass filter can also be used as a reflectance lamp. The lighting system may also include a micro discharge lamp (MDL)-high intensity ultraviolet light. LEDs, a laser, or a pressurized vapor lamp can be used for fluorescence excitation. The system may further include long pass filters and a variety of other lighting and camera accessory equipment, as required to elicit reflectance, fluorescence, or other illumination-related responses useful in detecting defects and/or contamination on the inspected object 20.

In operation, the position of the camera 30 IFOV (as defined by the area 18) is coordinated with the rotation of the object 20 and the placement of the helical guides 32, 34, 36, 38 so that the IFOV captures a selected number of rotations of the object 20, as the object 20 travels along the conveyances 12, 14 and is illuminated by (at least) the fluorescent and reflectance lighting systems.

In the preferred embodiment, the processor 40 receives image data from the camera 30 and assembles a concatenated line scan image of each inspected object 20. Processor 40 software automatically edits the assembled image data so that the data essentially comprises an "image cube" depicting all outer surfaces of the object 20, as the object 20 moves through the inspection system 10. The image cube data is then scrutinized based on pre-determined contamination and defect standards (expressed as contamination/defect thresholds). Examined objects 20 that are determined to meet the standards are retained for further processing, and objects 20 that are substandard are rejected.

In an alternative embodiment, the components of the inspection system 10 are essentially the same, however the relative positions of the downward 12 and upward 14 conveyances may be reversed. In this alternative embodiment, the upward conveyance 14 precedes the downward conveyance 12 in the tandem arrangement disclosed in the preferred embodiment. In this configuration, conveyances 12, 14 form an inverted "V", which may be advantageous in some inspection applications.

For the foregoing reasons, it is clear that the method and apparatus described herein provides an innovative system for inspecting three-dimensional objects, preferably spheroidal objects on a conveyance line. The system may be modified in multiple ways and applied in various technological applications. For example, although the method and apparatus described herein is generally directed to spheroidal food products, in alternative embodiments, the device may have some application to the inspection of non-spheroidal food or non-food items (such as manufactured products).

The method and apparatus described herein may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from this disclosure's spirit and scope, and all such modifications as would be obvious to one skilled in the art are intended to be included within the scope of the following claims.

What is claimed is:

1. An inspection system comprising:
   a rotating object;
   a downwardly-angled conveyance comprising:
   (a) a plurality of downwardly angled rotating members rotating the object in a first direction;
   (b) a helical guide encircling each one of the downwardly angled rotating members and guiding the object in a downward direction along the downwardly angled conveyance;
   an upwardly-angled conveyance comprising:
   (c) a plurality of upwardly angled rotating members rotating the object in the first direction;
   (d) a helical guide encircling each one of the upwardly angled rotating members and guiding the object in an upward direction along the upwardly angled conveyance;
   a camera obtaining images of the object, the upwardly angled and downwardly angled conveyances falling within an instantaneous field of view (IFOV) of the camera;
   a processor receiving the images of the object from the camera and producing object image data;
   wherein the inspection system is structured so that the object is retained or rejected based on the image data.

2. The inspection system of claim 1 wherein the downwardly angled conveyance is positioned in tandem with the upwardly angled conveyance.

3. The inspection system of claim 1 wherein the downwardly angled conveyance precedes the upwardly angled conveyance.

4. The inspection system of claim 1 wherein the system comprises a food inspection system.

5. The inspection system of claim 1 wherein the rotating object is a spheroid.

6. The inspection system of claim 1 wherein the rotating object comprises one of a fruit or a vegetable.

7. The inspection system of claim 1 wherein the plurality of downwardly angled rotating members comprises two elongated cylinders.

8. The inspection system of claim 7 wherein the two elongated cylinders are parallel.

9. The inspection system of claim 1 wherein the plurality of upwardly angled rotating members comprises two elongated cylinders.

10. The inspection system of claim 9 wherein the two elongated cylinders are parallel.

11. The inspection system of claim 1 wherein the camera comprises a digital line-scan camera.

12. The inspection system of claim 1 wherein the processor produces the image data in a form of a concatenated line scan image of an outer surface of the object.

13. The inspection system of claim 1 wherein the processor produces an image cube comprising an image of an outer surface of the object through at least one complete rotation of the object, the image cube showing outer surface defects and selected outer surface contamination on the object.

14. The inspection system of claim 13 wherein the defects on the outer surface of the object are apparent from a reflectance image of the object, and the contamination on the outer surface of the object is apparent from a fluorescence image of the object.

15. The inspection system of claim 1 wherein the system is structured so that a decision regarding whether to retain or reject the object is made after the object leaves the IFOV.

16. A method of inspecting an object, the method comprising the steps of:
   (a) providing an object;
   (b) conveying the object down a downwardly angled conveyance in a downward direction so that the object is rotated as it moves along, the downwardly angled conveyance comprising two parallel cylinders, a generally helical guide encircling each of the cylinders, the guides being structured to move the object along the downwardly angled conveyance;

(c) at an end of the downwardly angled conveyance, moving the object to an upwardly angled conveyance so that the object is rotated as the object moves in an upward direction along the upwardly angled conveyance, the upwardly angled conveyance comprises two parallel cylinders, a generally helical guide encircling each of the cylinders, each of the guides structured to move the object along the upwardly angled conveyance;

(d) positioning a digital line scan camera so that the IFOV of the camera includes at least a portion of the downwardly angled conveyance and the upwardly angled conveyance, the camera gathering image data for the object;

(e) communicating the image data from the camera to a processor; and, (f) making a decision regarding whether to retain or reject the object based on the image data.

17. The method of claim 16 wherein, in step (e), the processor produces an image cube comprising an image of an outer surface of the object through at least one complete rotation of the object, the image cube showing outer surface defects and selected outer surface contamination on the object.

\* \* \* \* \*